(12) United States Patent
Cermak et al.

(10) Patent No.: US 10,779,795 B2
(45) Date of Patent: Sep. 22, 2020

(54) LOW PROFILE ENDOCAVITY NEEDLE GUIDES

(71) Applicant: CIVCO Medical Instruments Co., Inc., Kalona, IA (US)

(72) Inventors: Craig Joseph Cermak, Riverside, IA (US); Timothy Meder, Riverside, IA (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 661 days.

(21) Appl. No.: 15/603,879

(22) Filed: May 24, 2017

(65) Prior Publication Data

US 2017/0340308 A1    Nov. 30, 2017

Related U.S. Application Data

(60) Provisional application No. 62/340,737, filed on May 24, 2016.

(51) Int. Cl.

| A61B 8/08 | (2006.01) |
|---|---|
| A61B 17/34 | (2006.01) |
| A61B 8/00 | (2006.01) |
| A61B 8/12 | (2006.01) |
| A61B 1/00 | (2006.01) |
| A61B 17/00 | (2006.01) |

(52) U.S. Cl.
CPC .......... *A61B 8/0841* (2013.01); *A61B 1/0014* (2013.01); *A61B 8/12* (2013.01);
(Continued)

(58) Field of Classification Search
CPC ... A61B 8/0841; A61B 8/4483; A61B 1/0014; A61B 8/12; A61B 8/4455;
(Continued)

(56) References Cited

U.S. PATENT DOCUMENTS 6,884,219 B1 * 4/2005 Pruter ................. A61B 8/0833
600/459
9,149,251 B2  10/2015 Steffen
(Continued)

OTHER PUBLICATIONS

International Search Report and Written Opinion issued in corresponding International Application No. PCT/US2017/034179, dated Aug. 30, 2017, 13 pages.

*Primary Examiner* — Theodore J Stigell
*Assistant Examiner* — Sean A Frith
(74) *Attorney, Agent, or Firm* — Snyder, Clark, Lesch & Chung, LLP

(57) ABSTRACT

A low profile endocavity needle guide device for an ultrasonic probe is disclosed. The device includes a needle guide and a clamp assembly. The needle guide is a tubular member configured to enable an elongated needle to be extended through it. The clamp assembly includes a first clamp member, a second clamp member and a slidable member. The first clamp member is pivotable with respect to the second clamp member between an engagement position and a release position, and vice versa. The slidable member is mounted on the first clamp member and includes a low profile projection which engages a ramped surface of the first clamp member to pivot the first clamp member to the engagement position when the projection is slid up the ramped surface, and to enable the first clamp member to move to the release position when the projection is slid down the ramp surface.

18 Claims, 4 Drawing Sheets

(52) U.S. Cl.
CPC .......... *A61B 8/4455* (2013.01); *A61B 8/4483* (2013.01); *A61B 17/3403* (2013.01); *A61B 2017/00292* (2013.01); *A61B 2017/00477* (2013.01); *A61B 2017/3413* (2013.01)

(58) Field of Classification Search
CPC ...... A61B 17/3403; A61B 2017/00292; A61B 2017/00477; A61B 2017/3413
See application file for complete search history.

(56) References Cited

U.S. PATENT DOCUMENTS

| | | | | |
|---|---|---|---|---|
| 9,850,013 | B2* | 12/2017 | Grant | B65B 39/007 |
| 2008/0171940 | A1 | 7/2008 | McGahan | |
| 2008/0221453 | A1* | 9/2008 | Suri | A61B 8/12 |
| | | | | 600/459 |
| 2011/0146091 | A1* | 6/2011 | Spaulding | G01C 9/26 |
| | | | | 33/372 |
| 2011/0218444 | A1* | 9/2011 | Steffen | A61B 8/0833 |
| | | | | 600/461 |
| 2012/0160863 | A1* | 6/2012 | Thompson | B65D 83/0409 |
| | | | | 221/8 |
| 2013/0137979 | A1* | 5/2013 | Deckman | A61B 8/4461 |
| | | | | 600/439 |
| 2013/0161363 | A1* | 6/2013 | Johnson | A45F 5/004 |
| | | | | 224/162 |
| 2016/0022309 | A1* | 1/2016 | Allaway | A61B 8/0841 |
| | | | | 600/464 |
| 2016/0113621 | A1* | 4/2016 | Deckman | A61B 8/4461 |
| | | | | 600/439 |

* cited by examiner

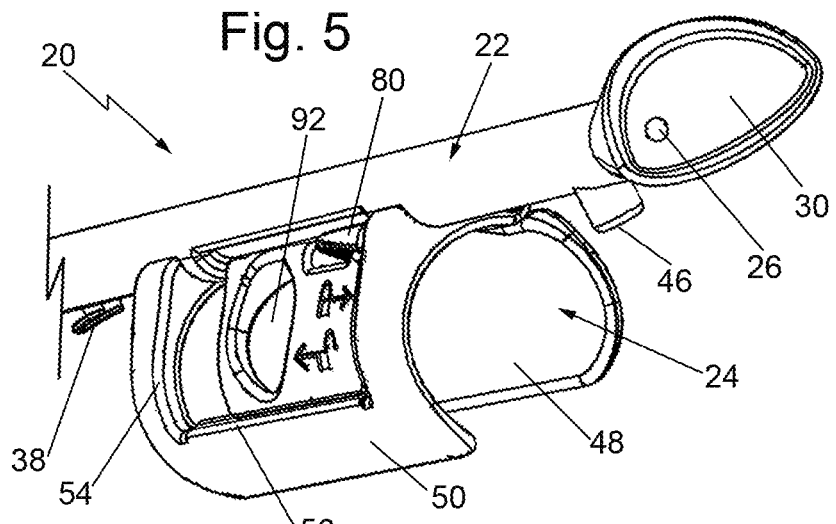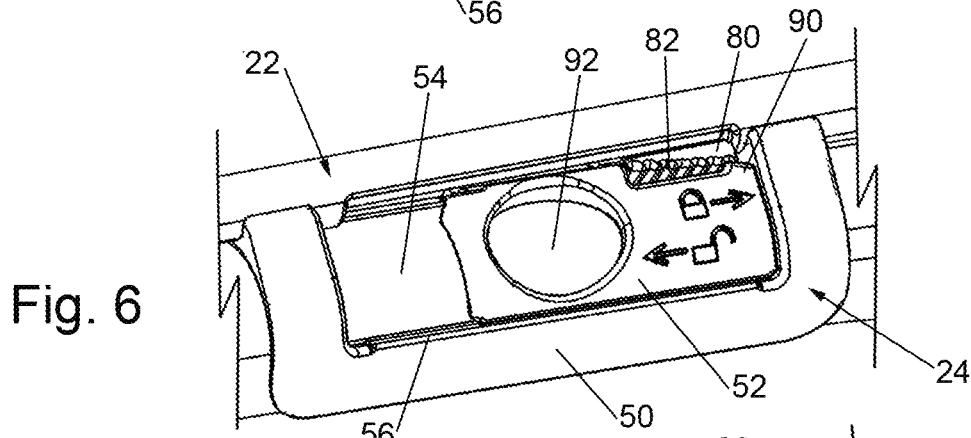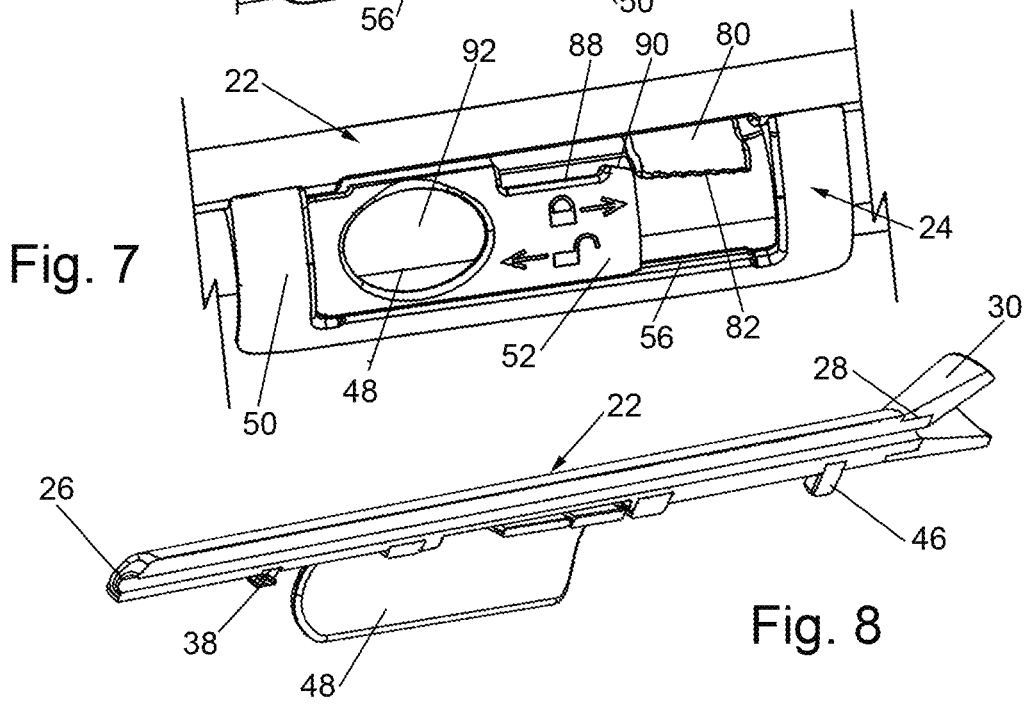

Fig. 9
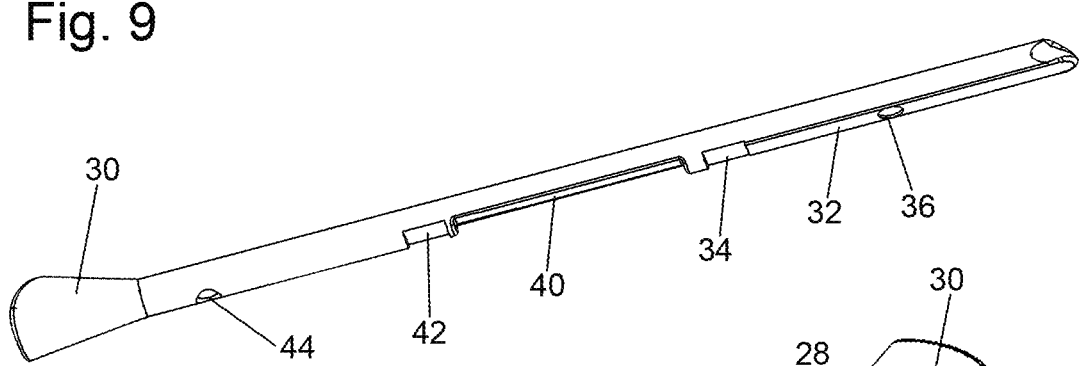
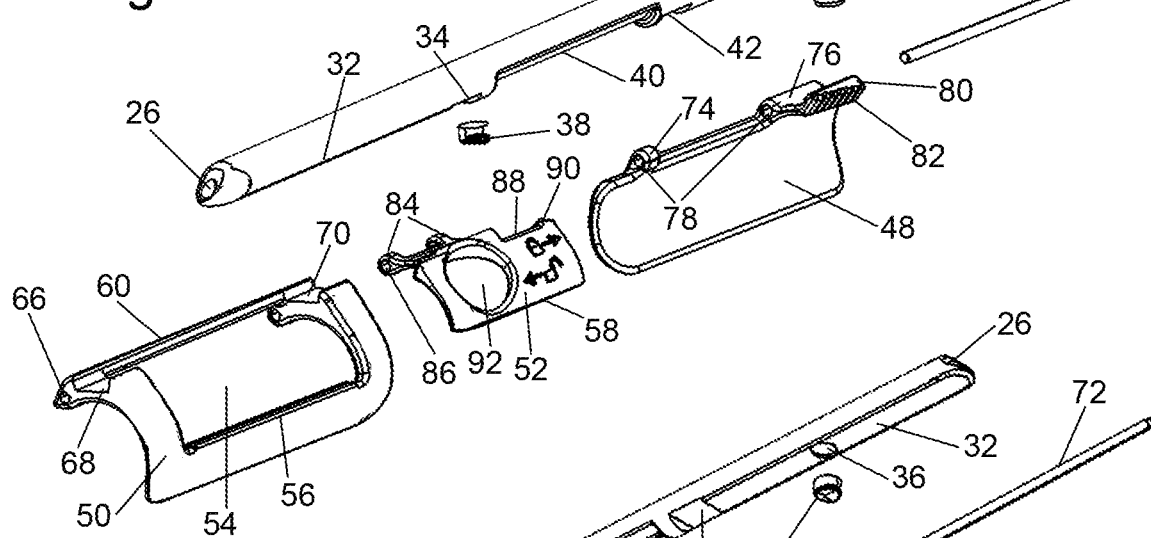
Fig. 10
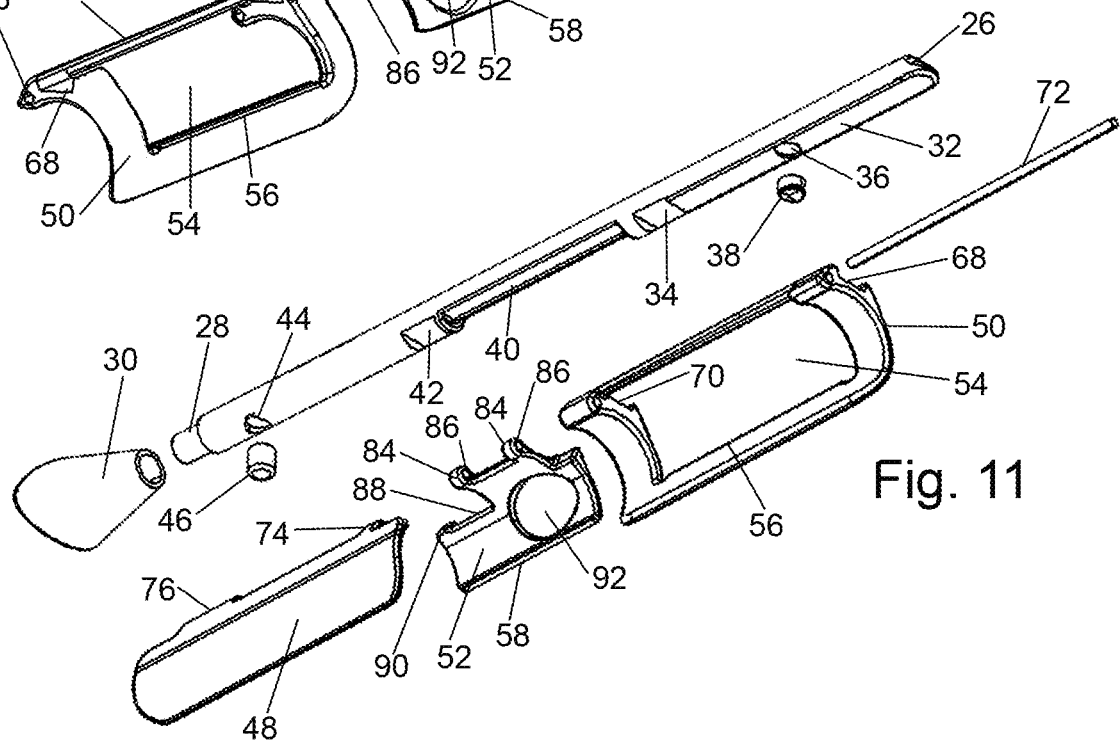
Fig. 11

LOW PROFILE ENDOCAVITY NEEDLE GUIDES

CROSS-REFERENCE TO RELATED APPLICATIONS

This application claims priority under 35 U.S.C. § 119 based on U.S. Provisional Patent Application No. 62/340,737 filed May 24, 2016, the disclosure of which is hereby incorporated by reference herein.

FIELD OF THE INVENTION

This invention relates generally to needle guides for medical imaging instruments and more particularly to devices for guiding needles into selected locations of a patient relative to a medical instrument imaging sensor.

BACKGROUND OF THE INVENTION

Imaging transducers, such as ultrasound probes, have become an accepted modality for exploring endocavities, e.g., the human digestive and reproductive tracts, of humans and animals in order to conduct routine examinations, as well as to identify evidence of tumors. In particular, using ultrasound, these tumors can be located and assessed. In conjunction therewith it is frequently desirable and even essential that biopsy samples of the tissue or fluid of a suspected tumor be removed for analysis. To that end, biopsy samples may be taken by carefully directing a hand-held needle, such as a biopsy instrument, catheter, or other thin instrument (hereafter referred to collectively as "needle" or "needles") into the body of a patient in order to remove a tissue sample. It is normally desirable that the needle be guided to a specific position within the body. Unfortunately, hand-held direction of a needle is often inadequate, being both inaccurate and time consuming. Thus, various needle guide devices have been designed for use with ultrasonic probes to assist in directing needles during imaging analysis.

Various means have been used commercially for securing endocavity guides to an ultrasound probe. For example commercially available endocavity needle guides frequently make use of either a hinged clamp with a thumbscrew to releasably secure the guide to the probe or use a hinged clamp with an over-center latch or a spring clip to releasably secure the needle guide to the probe. Those clamping mechanisms typically extend relatively far outward so that the resulting structure leaves something to be desired from the standpoint of being of a low profile. For example, in U.S. Pat. No. 9,149,251 (Steffen), which is assigned to the same assignee as this invention, and whose disclosure is incorporated by reference herein, there is disclosed a reusable endocavity needle guide. The needle guide basically comprises at least a first and second guide members and a mounting (e.g., clamp) assembly to releasably mount the needle guide on the probe. The clamp assembly makes use of a pivotable clamping member adapted to engage the probe and an outwardly extending thumb screw to secure the clamping member in place in engagement with the probe. Moreover, most prior art endocavity needle guides require the use of two hands to lock the needle guide to the probe in its desired orientation.

Hence, there is a need in the prior art for an endocavity needle guide device which overcomes those disadvantages of the prior art. The subject invention addresses that need by providing a needle guide that exhibits a low profile for ready insertion into the body of a patient with minimal discomfort, which is simple in construction, effective and which enables a user to mount the needle guide on the transducer and lock it in place with one hand.

BRIEF SUMMARY OF THE INVENTION

In accordance with one aspect of this invention there is provided an endocavity needle guide device configured for releasable mounting on an imaging transducer. The imaging transducer has a longitudinally extending distal portion having a central longitudinal axis and a peripheral outer surface. The needle guide device comprises an assembly of a needle guide and a clamp assembly. The needle guide comprises an elongated tubular member having a distal end, a proximal end, and a central passageway extending fully therethrough from the proximal end to the distal end. The passageway has a central longitudinal axis and is configured to enable an elongated needle or other elongated device to be extended therethrough, whereupon the central longitudinal axis of the needle guide is at a predetermined orientation with respect to the central longitudinal axis of the imaging transducer. The clamp assembly comprises a first clamp member, a second clamp member and a slidable member. The first clamp member has an inner surface. The second clamp member has an inner surface. The first clamp member is pivotable with respect to the second clamp member about a pivot axis extending parallel to the central longitudinal axis of the needle guide from an engagement position to a release position, and vice versa. The inner surfaces of the first and second clamp members tightly engage portions of the peripheral outer surface of the longitudinally extending distal portion of the imaging transducer when the clamp members are in the engagement position to releasably secure the needle guide to the imaging transducer. The slidable member is slidable with respect to the central longitudinal axis from a first position to a second position and vice versa. The slidable member is configured when in the first position to bring the clamp members in the engagement position.

In accordance with one preferred aspect of this invention the position of the first clamp member to the second clamp member when in the engagement position is adjustable to accommodate transducers having distal portions of different size cross sections.

In accordance with another preferred aspect of this invention the first clamp member includes a ramped surface and wherein the slidable member includes a projecting portion configured to slide along the ramped surface as the slidable member is moved between the first and second positions.

In accordance with another preferred aspect of this invention the sliding of the projecting portion up the ramped surface causes the pivoting of the first clamping member towards the second clamping member, and the sliding of the projecting portion down the ramped surface enables the pivoting of the first clamping member away from the second clamping member.

In accordance with another preferred aspect of this invention the ramped surface includes a plurality of respective notches spaced from one another along at least a portion of the ramped surface. Each of the notches is configured to receive the projecting portion of the slidable member to releasably secure the slidable member with respect to the ramped surface.

In accordance with another preferred aspect of this invention one of the needle guide device and the imaging transducer includes a stand-off projection and the other of the needle guide and the imaging transducer includes a recess for receipt of the stand-off projection to locate the needle guide at a desired position on the distal portion of the imaging transducer.

In accordance with another preferred aspect of this invention the needle guide device includes the stand-off projection and the imaging transducer includes the recess for receipt of the stand-off projection.

In accordance with another preferred aspect of this invention the proximal end of the elongated tubular member is generally funnel shaped to facilitate the introduction of the elongated needle or other elongated device to be extended into and through the central passageway.

In accordance with another preferred aspect of this invention the slidable member includes a user engaging portion configured to be engaged by a finger of a user to slide the slidable member from the first to the second position, and vice versa.

BRIEF DESCRIPTION OF THE DRAWINGS

FIG. 5 is a reduced size isometric view taken from the rear of the needle guide device with its clamp assembly in the closed state;

FIG. 6 is an enlarged isometric view of the clamp assembly portion of the needle guide device with that assembly is in its closed state;

FIG. 7 is an enlarged isometric view of the clamp assembly portion of the needle guide device with that assembly is in its opened state;

FIG. 8 is a reduced isometric view, in longitudinal section, of the needle guide of FIG. 1;

FIG. 9 is another isometric view, but not in section, of the needle guide of FIG. 1;

FIG. 10 is an exploded isometric view of the various components making up the needle guide device of FIG. 1;

FIG. 11 is another exploded isometric view of the various individual components making up the needle guide device of FIG. 1, but taken from a different angle;

DETAILED DESCRIPTION OF THE PREFERRED EMBODIMENTS

Figure 1:
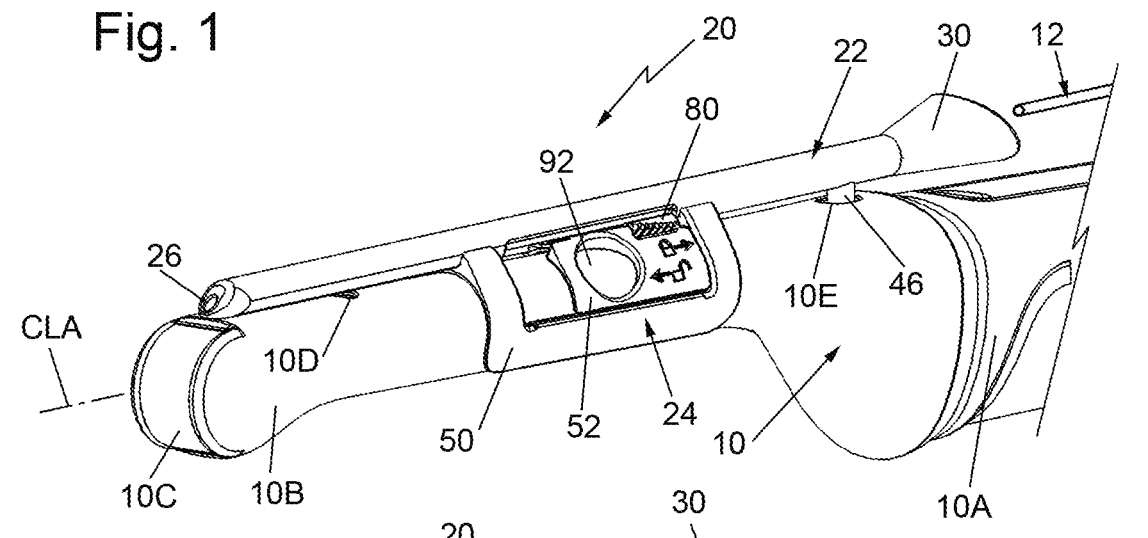
FIG. 1 is an isometric view of an exemplary imaging transducer, e.g., an ultrasonic probe, on which one exemplary embodiment of an endocavity needle guide device constructed in accordance with this invention is shown mounted and releasably secured in place on the transducer, and with the needle guide device comprising a needle guide and a clamp assembly.

Referring now to the various figures of the drawing wherein like reference characters refer to like parts, there is shown in FIG. 1 one exemplary low profile needle guide device 20 constructed in accordance with this invention. The needle guide device 20 is arranged to be releasably mounted on an imaging instrument 10, e.g., an ultrasound transducer or probe, to guide a needle 12 through a desired path for tissue biopsy or any number of medical procedures within an endocavity of a patient (human or animal). It should be pointed out at this juncture that the term "needle" as used herein means any type of elongated needle, biopsy instrument, catheter, or other thin instrument, that is arranged to be guided to a position inside the body of a patient for performing some type of procedure therein.

The needle guide device 20 basically comprises a needle guide 22 and a clamp assembly 24. The needle guide 22 will be described in detail later. Suffice it for now to state that it is an elongated tubular member having a central passageway 26 configured for receiving the needle 12 to provide a path that is orientated at a desired orientation, e.g., close to and parallel, to the central longitudinal axis CLA of the transducer or probe 10. The clamp assembly 24 will also be described in detail later. Suffice it for now to state that it is in the form of a low-profile clamshell-like clamp for releasably mounting the needle guide 22 on the distal portion of the imaging transducer.

Before describing the details of the device, a brief description of the imaging transducer or probe 10 is in order. To that end, it can be seen that the transducer 10 shown in the drawings is a conventional type, i.e., a Model IC9-RS probe of G.E. Healthcare. That transducer includes a proximal portion 10A which serves as a handle arranged to be held within the hand of a user. The distal portion 10B of the probe 10 terminates at a somewhat enlarged working end 10C at which the transducer's lens is located. The outside diameter of the distal portion 10B is significantly less than that of the handle 10A and less than the working end 10C. In the exemplary embodiment the distal portion 10B is of generally circular outer profile extending about the central longitudinal axis CLA. The upper surface of the distal portion 10B of the transducer close to the working head 10C includes a first locating recess 10D. A second locating recess 10E located is located on the upper surface of the transducer adjacent the interface of the distal portion 10B and the proximal portion 10A. The recesses 10D and 10E are configured for receipt of respective correspondingly shaped positioning or locating projections (to be described later) of a needle guide 22 to ensure that the needle guide device 20 will be mounted on the transducer 10 at the desired position, e.g., proximally of the transducer's lens.

It should be pointed out at this juncture that the exemplary needle guide device 20 shown is designed specifically for the particular transducer 10 shown. However, it should be clear that the subject invention contemplates needle guide devices that can be used with any manufacturer's ultrasound transducers (or other imaging instruments). Thus, each needle guide device of this invention can be designed to be transducer-specific, i.e., be configured to mate with a particular transducer. In fact with some modest modification to the needle guide devices of this invention, it is contemplated that they can be constructed to be universal to accommodate various types and models of imaging transducers. Irrespective of whether or not the devices are transducer specific or more universal, each of the needle guide devices of this this invention make use of a clamping assembly that is configured to enable the needle guide device to be mounted on transducers having distal end portions of different diameters or different shapes for releasably mounting the needle guide adjacent the working end of the transducer.

Turning now to FIGS. 5 and 8-11, the details of the needle guide 22 will now be described. As mentioned earlier the needle guide 22 elongated tubular member having a central passageway 26 extending therethrough. The distal end of the needle guide 22 is somewhat rounded to be atraumatic and is open, i.e., the distal end of the passageway 26 terminates at the distal end of the guide member. The proximal end of the needle guide 22 includes an annular necked down recess 28 (FIG. 10) for receipt of a flared hollow member 30. The member 30 has an open forward end which is undercut and which mates with the recess 28 to fixedly secure the flared hollow member 30 to the proximal end of the elongated needle guide. Thus, the proximal end of the needle guide is of a funnel like shape, the nadir of which constitutes the entryway to the passageway 26. As such the member 30 serves to direct a needle 12 or other elongated small diameter instrument into the passageway 26, so that it can pass down the passageway, whereupon the sharpened distal end of the needle 12 will exit the distal end of the needle guide.

As best seen in FIGS. 9 and 11, the needle guide 22 includes a flattened undersurface 32 located contiguous with the distal end and extending backward toward the center of the guide member. The proximal end 34 of the flattened undersurface 32 is configured to receive a portion of the clamp assembly 24, as will be described later. A hole 36 is located in the undersurface 32 and is configured to receive a slotted stand-off or locator pin 38 so that the pin will project downward from the undersurface for a short distance. The pin 38 is fixedly secured in the hole 36 and is arranged to be releasably received within the locator hole 10D in the transducer when the device 20 is mounted thereon. A second flattened undersurface 40 is located at the bottom of the needle guide 22 immediately proximally of the flattened undersurface 34. The flattened undersurface 40 is also configured to receive portions of the components making up the clamp assembly 24, as will be described later. A third and very short length flattened undersurface 42 is located at the bottom of the needle guide 22 immediately proximally of the flattened undersurface 40. The flattened undersurface 42 is also configured to receive a portion of the clamp assembly 24, as will be described later. A second hole 44 is located on the rounded undersurface of the needle guide 22 closely adjacent the funnel 30. The hole 44 is configured to receive a stand-off or locator pin 46 so that the pin 46 will project downward from the undersurface for a short distance. The pin 46 is fixedly secured in the hole 44 and is arranged to be releasably received within the locator hole 10E in the transducer when the device 20 is mounted thereon. Thus, the pins 38 and 46 cooperate with the holes 10D and 10E, respectively, to precisely position the needle guide device 20 on the transducer 10 at the desired position so that the passageway 26 in the needle guide is parallel to and clearly adjacent the longitudinal central axis CLA of the transducer 10.

Turning now to FIGS. 3-5, 10 and 11, the details of the clamp assembly 24 for releasably securing the needle guide 22 onto the transducer 10 at the positions established by the pins 38 and 46 and locating holes 10D and 10E, respectively, will now be discussed. To that end, it can be seen that the clamp assembly 24 basically comprises a first clamp member 48, a second clamp member 50, and a slidable locking member 52 (which is also referred to as a "slide lock"). The first clamp member 48 is a generally arcuate shaped, somewhat elongated body having an arcuate inner surface 48A. In this case the inner surface 48A forms a portion of a circular surface. The second clamp member 50 is also a generally arcuate shaped somewhat elongated body having an arcuate inner surface 50A. In this case the inner surface 50A also forms a portion of a circular surface, with the radius of the two surfaces 48A and 50A being the same. The two clamp members 48 and 50 are of approximately the same size and length. The wall making up of the first clamp member 48 is solid, whereas the wall of the second clamp member 50 includes a generally rectangular window 54 in it. The window 54 is configured to slidably receive the slide lock 52. To that end, as best seen in FIGS. 5-7, slide lock 52 is in the form of an arcuate wall of a generally rectangular profile. The radius of curvature of the arcuate wall of the slide lock 52 is approximately the same as that of the clamp member 50. The lower edge of the window 54 is in the form of an elongated linear track 56 for slidable receipt of the lower edge 58 of the slide lock 52.

Figure 12:
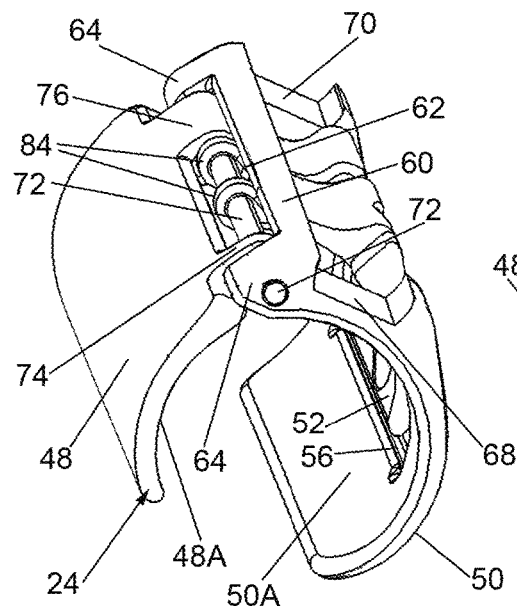
FIG. 12 is an enlarged isometric view of the clamp assembly of the needle guide device of FIG. 1.
Figure 13:
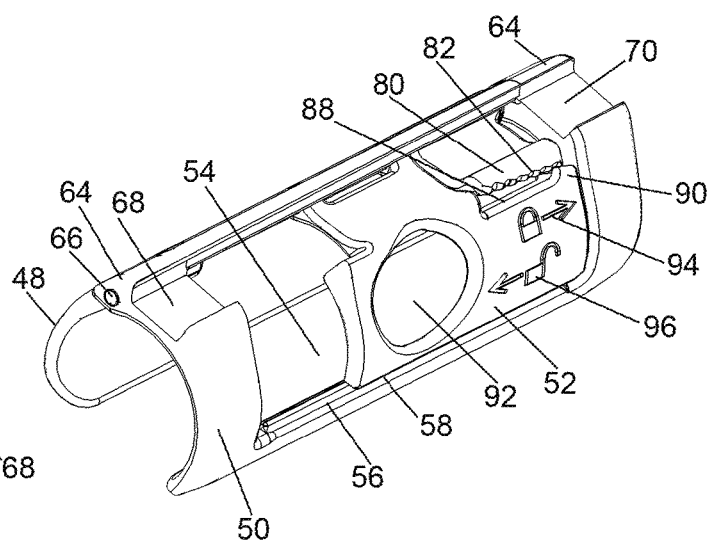
FIG. 13 is another enlarged isometric view of the clamp assembly of the needle guide device of FIG. 1, but taken from a different angle.
Figure 14:
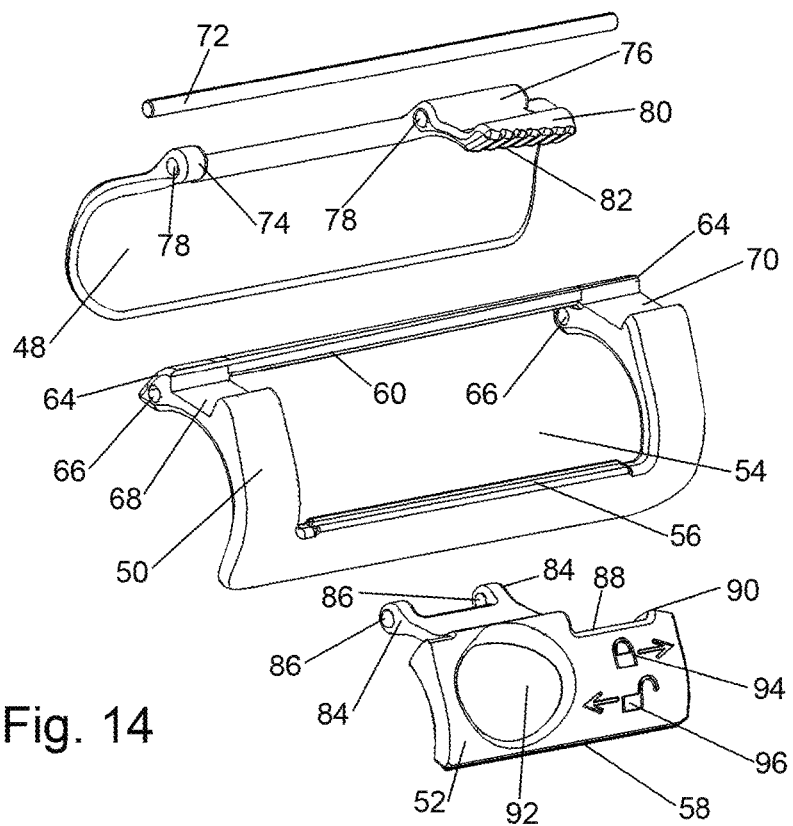
FIG. 14 is an exploded isometric view of the individual components making up the clamp assembly of the needle guide device of FIG. 1.

As best seen in FIGS. 12-14, the upper edge of the second clamp member 50 is in the form of an elongated thickened wall 60, the central portion of which is undercut at 62 (FIG. 12). The end portions 64 of the thickened wall 60 include respective passageways 66 extending through them and which are axially aligned. The portions of the second clamp member 50 contiguous with the ends of that clamp member and immediately adjacent the elongated thickened wall 60 are in the form of respective planar notches 68 and 70. The notches 68 and 70 are configured to receive the undersurfaces 34 and 42, respectively, of the needle guide 22 to fixedly secure the needle guide 22 to the clamp member 50. Thus, the second clamp member 50 is held stationary with respect to the needle guide 22.

The passageways 66 extending through the end portions 64 of the thickened wall 60 are configured to receive respective portions of an elongated pivot rod 72. The rod 72 serves to pivotably connect the first clamp member 48 to the second clamp member 50, such that the first clamp member 48 can be pivoted with respect to the stationary second clamp member 50. To that end, as best seen in FIGS. 10 and 14 the upper edge of the first clamp member 48 is in the form of two projecting ears 74 and 76. Each ear includes a passageway 78 extending through it and which are axially aligned with each other. The ears 74 and 76 are configured to be located in the undercut portion 62 of the thickened wall 60 of the second clamp member 50 with the passageways 78 of those ears axially aligned with the passageways 66 of the second clamp member 50. Accordingly, the pivot rod 72 can be extended through those aligned passageways to form a hinge pivotally connecting the pivotable first clamp member 48 to the stationary second clamp member 50, whereupon the first clamp member can be pivoted about the longitudinal axis of the pivot rod 72.

As best seen in FIGS. 6, 7, 13 and 14 a tab 80 projects radially outward from the ear 76 and hence outward from the pivot axis formed by the pivot rod 72. However, as can be seen clearly from the end views of FIGS. 3 and 4, the tab 80 does not extend substantially beyond the outer surface of the clamp member 50. In fact, in the exemplary embodiment shown it doesn't extend beyond the outer surface of the clamp member 50, at all. However, it is contemplated that the tab 80 could extend slightly beyond the outer surface of the clamp member, so long as it still results in a low profile configuration. The tab 80 includes a free end in the form of a wedge shaped member having a ramped undersurface 82, the plane of which slopes at a shallow acute angle to the axis of the pivot rod. The ramped undersurface includes a plurality of equidistantly spaced rounded notches or grooves along the length thereof. The notches or grooves extend generally perpendicularly to the axis of the pivot rod 72. The notched undersurface 82 of the first clamp member 48 is arranged to be engaged by a projecting portion, to be described shortly, of the slide lock 52 to effect the pivoting of the first clamp member with respect to the second clamp member when the slide lock is slid within the window.

The upper edge of the slide lock 52 is in the form of two projecting ears 84 which are spaced apart from each other and located in the portion of the slide lock closest to the distal end thereof. Each ear includes a passageway 86 extending through it and which are axially aligned with each other. The ears 84 are configured to be located in the undercut portion 62 of the thickened wall 60 of the second clamp member 50, with the passageways 86 of those ears axially aligned with the passageways 66 of the second clamp member 50. Accordingly, the pivot rod 72 can be extended through those aligned passageways. The spacing between the ears 84 and 86 is less than the spacing between the ears 74 and 76 of the first clamp member 48. Hence the slide lock 52 can be slid along the pivot rod 72 and along the track 56 of the window 54 in the second clamp member between a first or engagement position and a second or release position, and vice versa. When the slide lock 52 is in the first or engagement position, its proximal end will be located immediately adjacent the proximal end of the window 54, as best seen in FIG. 6. When the slide lock 52 in in the second or release position its distal end will be located immediately adjacent the distal end of the window 54, as best seen in FIG. 7. The edge 58 of the slide lock 52 is configured to mate with the track 56 at the bottom of the window 54 to prevent the slide lock from swinging outward from the window.

The upper edge of the slide lock proximally of the ears 84 is in the form of a notch 88 the notch is linear as best seen in FIG. 6. A wedge-shaped projection 90 extends outward from the top edge of the slide lock 52 immediately proximally of the notch 88. The apex of the projection 90 is configured to slide along and engage the ramped surface as the slide lock 52 is slid between its first and second positions and vice versa. As should be appreciated by those skilled in the art that action will cause the pivoting of the first clamp member 48 either toward or away from the second clamp member, depending upon the direction which the slide lock is slid. Thus, when the needle guide is being mounted on a probe whose distal portion is of the smallest diameter that the needle guide can accommodate and the slide lock 52 is slid to the first or engagement position, the projection 90 will slide upward along the ramp surface 82 and will be located in the most proximally located groove in that surface, like shown in FIG. 6. It should be appreciated by those skilled in the art, that the position of the slide lock 52 when locked will vary based upon the size (diameter) of the distal portion of the probe. Thus, with a small diameter probe, the side lock 52 may lock into the most proximally located groove position, whereas a probe with a larger diameter distal portion probe will require the slide lock to engage a groove closer to the first engagement position.

Figure 2:
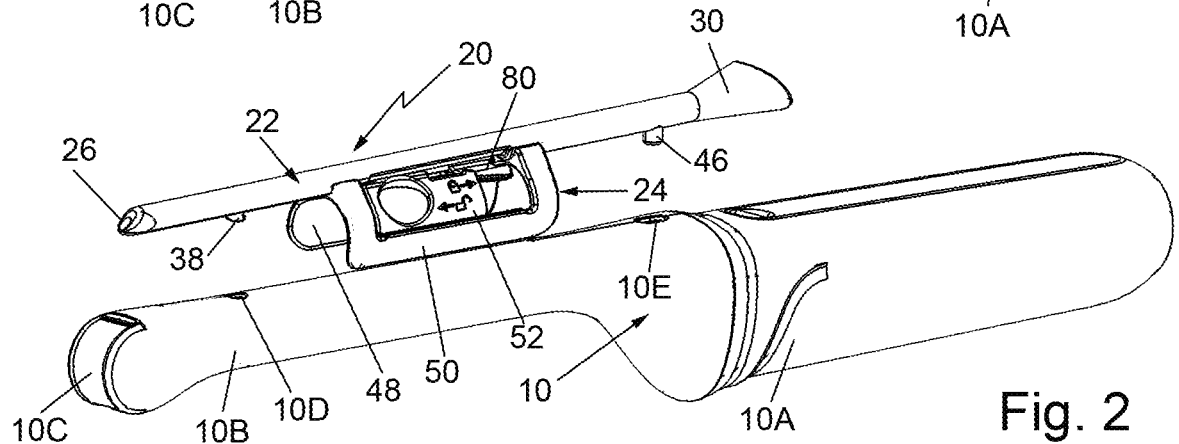
FIG. 2 is a slightly reduced exploded isometric view of the needle guide device and the transducer shown in FIG. 1, with the clamp assembly being shown in its open state so that the needle guide device can be mounted and secured to the transducer.
Figure 3:
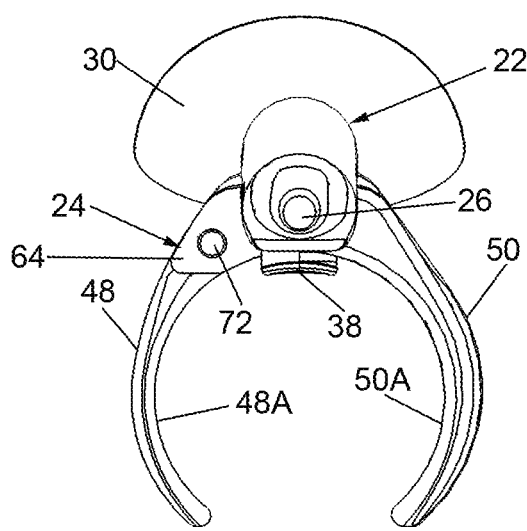
FIG. 3 is an enlarged front elevational view of the needle guide device of FIG. 1 with its clamp assembly shown in its closed state, which is the state shown in FIG. 1, wherein the needle guide device is mounted and releasably secured on the imaging transducer.
Figure 4:
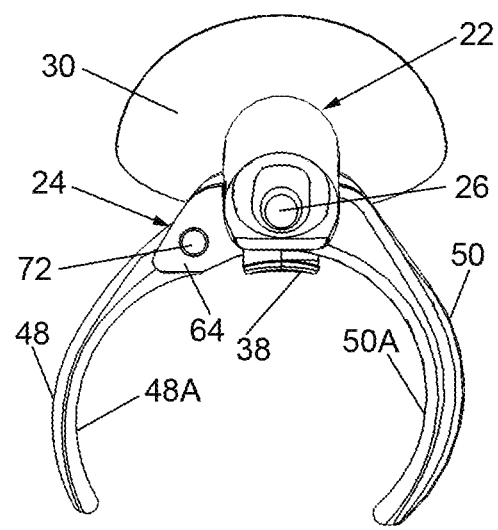
FIG. 4 is an enlarged front elevational view of the needle guide device with its clamp assembly shown in its opened state, such as the state shown in FIG. 2, wherein the needle guide device is ready to be mounted on the imaging transducer.

The sliding action of the projection up the ramp surface to the appropriate notch (e.g., in the example shown that notch is the most proximally located notch in that ramped surface), has the effect of pivoting the first clamp member in a rotational direction toward the stationary second clamp member, whereupon the peripheral surface of the distal portion 10B of the transducer 10 will be tightly clamped between the inner surfaces 48A and 50A of the clamp members 48 and 50, respectively, like shown in FIG. 1. Conversely, when the slide lock 52 is slid to the second or release position, like shown in FIG. 7, the projection 90 will slide downward along the ramp surface, thereby releasing the first clamp member to enable it to be pivoted in the opposite rotational direction, i.e., away from the stationary second clamp member. This action will have the effect of releasing the inner surfaces 48A and 50A of the clamp members from the peripheral surface of the distal portion 10B of the transducer, thereby enabling the needle guide device 20 to be dismounted from the transducer as shown in FIG. 2.

As should also be appreciated by those skilled in the art if the projection 90 of the slide lock is slid to any intermediate position on the ramped surface 82 between the proximal end of the ramped surface and the distal end of that surface, the pivotable first clamp member 48 will be pivoted toward the stationary second clamp member 50 by a corresponding amount. Hence by the appropriate positioning of the slide lock 52 the device 20 can accommodate transducers having distal end portions of different diameters. Moreover, since the engagement of the projection 90 with the sloped ramp surface is achieved by the releasable seating of the projection in the corresponding groove of the ramped surface that engagement acts as detent mechanism releasably locking the clamp member 48 at the corresponding pivotal orientation with respect to the stationary clamp member.

In order to facilitate the sliding of the slide lock 52 between the first and second positions and vice versa, the slide lock includes a finger hole 92 in its wall. Moreover, as can be seen best in FIG. 14 the outer surface of the slide lock includes indicia 94 in the form of a proximally directed arrow and associated "closed lock" icon to direct the user in the direction to slide the slide lock to secure the clamp assembly onto the transducer. The outer surface of the slide lock also includes indicia 96 in the form of a distally directed arrow and associated "open lock" icon to direct the user in the direction to slide the slide lock to release the clamp assembly from the transducer.

As should also be appreciated by those skilled in the art, owing to the construction of the needle guide device it can be locked in place on the imaging transducer by a user with only one hand and can also be unlocked for release from the imaging transducer using only one hand.

Use of the needle guide device 20 will now be described. If desired a thin, flexible sheath or other cover (e.g., a latex, condom-shaped sheath) can be placed over the ultrasonic transducer or probe 10 before the needle guide device 20 is mounted thereon to keep the instrument sanitary. To mount the needle guide device on the probe all that is required is the user to slide the slide lock 52 to the second or release position to pivot the pivotable clamp member 48 with respect to the stationary clamp member 50 to the open or release position. That action can be accomplished by the user with only one hand by inserting his/her finger into the finger hole 92 and pushing the slide lock in the distal direction. Once the clamp assembly is open, the user can place the needle guide device on the transducer such that the locating pins 38 and 46 are aligned with and inserted into the locating holes 10D and 10E, respectively. The slide lock 52, can then be slid in the proximal direction by the user inserting his/her finger into the finger hole 92 and sliding the slide lock proximally, whereupon the projection 90 slides upward on the ramped surface 82 until the inner surfaces 48A and 50A of the clamp members tightly engage respective portions of the periphery of the distal portion 10B of the probe. That action may occur at any point along the ramped surface, depending upon the diameter of the distal portion of the probe.

The probe with the needle guide device thereon is now ready for use. To that end, the probe with the needle guide thereon is inserted as a unit through a natural orifice, e.g., into the rectum, so that the proximal portion of the needle guide is located just outside of the patient. Since the slide lock is flush with the outer surface of the second clamp member and thus does not extend outward therefrom this provides a very low profile needle guide. Accordingly, it can be inserted into the patient easily and with minimal patient discomfort. Moreover the flattened undersurfaces of the needle guide 22 enable it to be located very close to the distal end portion of the probe so that the central passageway 26 is located closer to the central longitudinal axis CLA of the probe. This further reduces the combined profile of the portion of the needle guide device and the distal portion of the probe on which it is mounted and which will be inserted into the body of the patient, while also aiding the physician to direct the needle 12 to the anatomy of interest under the guidance provided by the image produced by the probe. In particular, when the probe has imaged an area of interest, e.g., an area of the prostate to be biopsied, the needle 12 can be inserted into the funnel shaped member 30 of the needle guide 22 mounted on the probe. The needle can then be extended through the passageway 26 until the distal end of the needle 12 extends beyond the free end of the needle guide 22 and is at the desired position to take the biopsy sample all the while the probe 10 will provide images of the movement of the needle to and into that tissue. Once the biopsy procedure has been completed the needle 12 can be removed by withdrawing it from the needle guide device 20. The probe 10 and the needle guide 20 can then be removed as a unit from the patient.

It should be pointed out at this juncture that the needle guide device 20 is merely exemplary of many needle guide devices that can be constructed in accordance with this invention to form a path for a needle or other elongated instrument dependent on the specific transducer requirement. In this regard the needle guide 22 has channel specific geometry to provide a path for needle guidance, with the size and geometry being dependent upon transducer geometry and needle path requirements.

The foregoing description of exemplary implementations provides illustration and description, but is not intended to be exhaustive or to limit the embodiments described herein to the precise form disclosed. Without further elaboration, the foregoing will so fully illustrate my invention that others may, by applying current or future knowledge, adopt the same for use under various conditions of service. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. An endocavity needle guide device configured for releasable mounting on an imaging transducer, the imaging transducer having a longitudinally extending distal portion having a first central longitudinal axis and a peripheral outer surface, said needle guide assembly comprising:

a needle guide comprising an elongated tubular member having a distal end, a proximal end, and a central passageway extending fully therethrough from said proximal end to said distal end, said passageway having a second central longitudinal axis, said passageway being configured to enable an elongated needle or other elongated device to be extended therethrough in a predefined path along said second central longitudinal axis of said needle guide, whereupon said second central longitudinal axis of said needle guide is at a predetermined orientation with respect to the first central longitudinal axis of said imaging transducer; and a low profile clamp assembly comprising a first clamp member, a second clamp member and a slidable member, said first clamp member having an inner surface and an outer surface, said second clamp member having an inner surface and an outer surface, said first clamp member being pivotable with respect to said second clamp member about a pivot axis extending parallel to said first central longitudinal axis from an engagement position to a release position, and vice versa, said inner surfaces of said first and second clamp members tightly engaging portions of said peripheral outer surface of the longitudinally extending distal portion of the imaging transducer when said clamp members are in said engagement position to releasably secure said needle guide to the imaging transducer, said slidable member being slidable in a direction parallel to said first central longitudinal axis from a first position to a second position, and vice versa, said slidable member being configured when in said first position to bring said clamp members in said engagement position, wherein said first clamp member includes a ramped surface and wherein said slidable member includes a projecting portion configured to slide along said ramped surface in a direction parallel to said first central longitudinal axis so as to cause the inner surface of said first clamp member to rotate about the pivot axis between the first position and the second position.

2. The needle guide device of claim 1, wherein said needle guide assembly is reusable.

3. The needle guide device of claim 1, wherein said slidable member is mounted on said first clamp member and configured so that it does not extend substantially beyond said outer surface of said first clamp member.

4. The needle guide device of claim 3, wherein said needle guide assembly is reusable.

5. The needle guide device of claim 1, wherein the sliding of said projecting portion up said ramped surface causes the pivoting of said first clamping member towards said second clamping member, and wherein the sliding of said projecting portion down said ramped surface enables the pivoting of said first clamping member away from said second clamping member.

6. The needle guide device of claim 5, wherein said ramped surface includes a plurality of respective notches spaced from one another along at least a portion of said ramped surface, with each of said notches being configured to receive said projecting portion of said slidable member to releasably secure said sliding member with respect to said ramped surface.

7. The needle guide device of claim 1, wherein said proximal end of said elongated tubular member is generally funnel shaped to facilitate the introduction of the elongated needle or other elongated device to be extended into and through said central passageway.

8. The needle guide device of claim 1, wherein said slidable member includes a user engaging portion configured to be engaged by a finger of a user to slide the slidable member from said first to said second position, and vice versa.

9. The needle guide device of claim 8, wherein the user engaging portion comprises a hole.

10. The needle guide device of claim 1, wherein one of said needle guide and the imaging transducer including a stand-off projection and the other of said needle guide and the imaging transducer including a recess for receipt of the stand-off projection to locate said needle guide at a desired position on said distal portion of the imaging transducer.

11. The needle guide device of claim 10, wherein said needle guide includes said stand-off projection and the imaging transducer including the recess for receipt of said stand-off projection.

12. The needle guide device of claim 1, wherein said proximal end of said elongated tubular member is generally funnel shaped to facilitate the introduction of the elongated needle or other elongated device to be extended into and through said central passageway.

13. The needle guide device of claim 1, wherein said slidable member includes a user engaging portion configured to be engaged by a finger of a user to slide the slidable member from said first to said second position, and vice versa.

14. The needle guide device of claim 13, wherein the user engaging portion comprises a hole.

15. The needle guide device of claim 1, additionally comprising first indicia indicating the direction for sliding said slidable member to said first position and second indicia indicating the direction for sliding said slidable member to said second position.

16. The needle guide device of claim 15, wherein said first indicia is located on said slidable member and wherein said second indicia is located on said slidable member.

17. The needle guide device of claim 1, wherein the peripheral outer surface of the elongated distal portion of the imaging transducer is arcuate, wherein said inner surface of said first clamping member is arcuate and said inner surface of said second clamping member is arcuate.

18. An imaging transducer including the needle guide device of claim 1.

* * * * *